United States Patent
Watson et al.

(10) Patent No.: US 10,136,897 B2
(45) Date of Patent: Nov. 27, 2018

(54) EXPANDABLE VASO-OCCLUSIVE DEVICES HAVING SHAPE MEMORY AND METHODS OF USING THE SAME

(71) Applicant: Boston Scientific Scimed, Inc., Maple Grove, MN (US)

(72) Inventors: Christopher Watson, Lincoln, MA (US); Alison Lepordo, North Andover, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 340 days.

(21) Appl. No.: 14/806,210

(22) Filed: Jul. 22, 2015

(65) Prior Publication Data

US 2016/0022270 A1  Jan. 28, 2016

Related U.S. Application Data

(60) Provisional application No. 62/027,298, filed on Jul. 22, 2014.

(51) Int. Cl.
*A61M 29/00* (2006.01)
*A61B 17/12* (2006.01)
*A61B 17/00* (2006.01)

(52) U.S. Cl.
CPC ......... *A61B 17/1214* (2013.01); *A61B 17/12* (2013.01); *A61B 17/1215* (2013.01); *A61B 17/12109* (2013.01); *A61B 17/12163* (2013.01); *A61B 2017/00867* (2013.01); *A61B 2017/00871* (2013.01); *A61B 2017/1205* (2013.01)

(58) Field of Classification Search
CPC ............... A61B 17/12; A61B 17/1214; A61B 17/12109; A61B 17/12163; A61B 17/1215; A61B 2017/1205; A61B 2017/00867; A61M 29/00
See application file for complete search history.

(56) References Cited

U.S. PATENT DOCUMENTS

| | | | | |
|---|---|---|---|---|
| 5,843,118 | A * | 12/1998 | Sepetka | A61B 17/12022 606/191 |
| 7,014,645 | B2 * | 3/2006 | Greene, Jr. | A61B 17/12022 606/158 |
| 2005/0283183 | A1 | 12/2005 | Tran et al. | |
| 2007/0239194 | A1 | 10/2007 | Tran et al. | |
| 2008/0097508 | A1 | 4/2008 | Jones et al. | |
| 2010/0069838 | A1 | 3/2010 | Weber et al. | |
| 2012/0158034 | A1 | 6/2012 | Wilson et al. | |
| 2012/0226304 | A1 | 9/2012 | Ryan et al. | |
| 2012/0323267 | A1 | 12/2012 | Ren | |
| 2013/0184658 | A1 | 7/2013 | Duncan | |

OTHER PUBLICATIONS

Lendlein et al., "Shape Memory Polymers", Angew. Chem. Int. ID., (2002), vol. 41, pp. 2034-2057.

\* cited by examiner

*Primary Examiner* — Victor Nguyen

(57) ABSTRACT

In some aspects, the present disclosure is directed to vaso-occlusive devices which include a device portion and one or more expandable components which include a shape memory material and which expand laterally outward from the device portion upon being subjected to an activating stimulus. Other aspects of the disclosure pertain to systems containing such devices and methods of forming vascular occlusions using such devices.

19 Claims, 3 Drawing Sheets

EXPANDABLE VASO-OCCLUSIVE DEVICES HAVING SHAPE MEMORY AND METHODS OF USING THE SAME

STATEMENT OF RELATED APPLICATION

This application claims the benefit of U.S. Ser. No. 62/027,298, filed Jul. 22, 2014 and entitled "EXPANDABLE VASO-OCCLUSIVE DEVICES HAVING SHAPE MEMORY AND METHODS OF USING THE SAME", which is hereby incorporated by reference in its entirety.

FIELD

The present disclosure relates to medical devices. More particularly, the present disclosure relates to vaso-occlusive devices and to methods and systems for performing vaso-occlusive procedures using such devices.

BACKGROUND

In many clinical situations, blood vessels are occluded for a variety of purposes, such as to control bleeding, to prevent blood supply to tumors, or to block blood flow within an aneurysm, among others. Various vaso-occlusive devices may be used for this purpose, including vaso-occlusive coils. Some vaso-occlusive coils include fibers that can, for example, enhance thrombosis at a treatment site.

SUMMARY

The present disclosure relates to vaso-occlusive devices and to methods and systems for performing vaso-occlusive procedures using such devices.

In one aspect, the disclosure provides vaso-occlusive devices which comprise an elongated device portion and one or more expandable components which comprise a shape memory material, wherein the one or more expandable components expand laterally outward from (i.e., expand outward relative to a longitudinal axis of) the elongated device portion upon being subjected to an activating stimulus.

An advantage of such vaso-occlusive devices is that they can be advanced into the vasculature of a subject in a low profile configuration (i.e., a configuration of reduced cross-sectional area) that enables or improves delivery of the devices through a constrained space (e.g., blood vessel, catheter, etc.), after which the expandable components can be deployed, thereby increasing the cross-sectional area of the devices and thus enhancing the ability of the devices to form a occlusions.

In certain aspects, the activating stimulus for expanding the expandable components may be a force wherein an expandable component that is compressed into a confined space is forced from the confined space and expands laterally outward (i.e., where the expandable component is an elastic component that behaves like a spring).

In addition or alternatively, in certain aspects, the activating stimulus for expanding the expandable components may be selected from one or more of the following, among others: thermal stimulus, electrical stimulus, chemical stimulus, pressure stimulus, or light stimulus. For example, the shape memory material may be activated by increase in temperature from below a thermal transition temperature of the shape memory material to above the thermal transition temperature of the shape memory material. In a particular aspect, the thermal transition temperature of the shape memory material may be between 30° C. and 37° C., or the thermal transition temperature of the shape memory material may be between 38° C. and 50° C.

Embodiments of any of the above aspects may include a shape memory material that is a shape memory polymer, a shape memory material that is a shape memory alloy (e.g., an alloy comprising nickel and titanium), or both.

Embodiments of any of the above aspects and embodiments may include an elongated device portion that comprises an elongated cylindrical portion. The elongated cylindrical portion may be in the form of, for example, a slotted tube or a coil, or it may be in another configuration.

Embodiments of any of the above aspects and embodiments may include an expandable component that comprises a sheet of shape memory material. For example, the devices of the present disclosure may comprise one or more of the following: a sheet of the shape memory material folded at a surface of the elongated device portion, a sheet of the shape memory material at least partially wrapped around the elongated device portion, or a sheet of shape memory material that comprises a plurality of apertures, among other possible configurations.

Embodiments of any of the above aspects and embodiments may include an expandable component that comprises a plurality of elongated segments of shape memory material. For example, the devices of the present disclosure may comprise one or more of the following: elongated segments that form an undulating pattern or elongated segments that form a helix or a portion thereof, including embodiments where a plurality of the elongated segments form oppositely wound helixes, or portions thereof.

Embodiments of any of the above aspects and embodiments may include a coating of thrombogenic material on at least a portion of the expandable components.

In some aspects, the present disclosure provides systems that include (a) a vaso-occlusive device in accordance with any of the preceding aspects and embodiments and (b) a catheter configured to introduce the vaso-occlusive device into the vasculature.

In some aspects, the present disclosure provides methods of forming vascular occlusions which comprise (a) advancing a vaso-occlusive device in accordance with any of the preceding aspects and embodiments to an implant location in a subject and (b) subjecting the shape memory material to an activating stimulus, thereby deploying the one or more expandable components in the subject. Subjects include, for example, mammalian subjects including human subjects, pets and livestock.

In certain particular aspects, a vaso-occlusive device is advanced to an implant location in a subject under conditions such that the shape memory material remains at a temperature that is below the thermal transition temperature of the shape memory material, and the vaso-occlusive device is released at the implant location under conditions such that the temperature of the shape memory material rises above the thermal transition temperature of the shape memory material thereby deploying the one or more expandable components in the subject.

An advantage of the present disclosure is that systems and methods are provided wherein vaso-occlusive devices can be advanced into the vasculature of a subject in a low profile configuration (i.e., a configuration of reduced cross-sectional area) that enables or improves delivery of the devices through a constrained space (e.g., blood vessel, catheter, etc.), after which expandable components of the devices are deployed via a shape memory effect by means of a suitable activating stimulus (e.g., a thermal stimulus, among others activating stimuli), thereby increasing the cross-sectional area of the devices and thus enhancing the ability of the devices to form occlusions.

The above and other aspects, embodiments and advantages of the present disclosure will become apparent to those of ordinary skill in the art upon review of the detailed description set forth below.

DETAILED DESCRIPTION

Figure 1A:
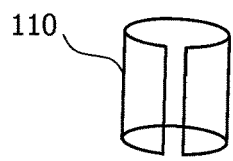
FIG. 1A and FIG. 1B are schematic illustrations of an expandable component in contracted and expanded configurations, respectively, according to an embodiment of the present disclosure.

Many clinical situations require a reduction in or complete stoppage of blood flow to some region of a subject's body. Vaso-occlusive devices are devices that are used to stop undesired blood flow, for example, to stop or prevent bleeding aneurysms, to stop abnormal blood flow in arteriovenous malformations (AVMs), to close a patent ductus arteriosus (PDA), to treat traumatic fistulae, or to perform tumor embolization, among other uses. These conditions require that the blood flow through a blood vessel or portion thereof be reduced and stopped, for example, by introducing the vaso-occlusive device into a body lumen to slow the flow and then allow the natural clotting process form a more complete blockage.

In the present disclosure, vaso-occlusive devices are provided which comprise one or more expandable components that have a low profile during delivery but which expand laterally outward subsequent to device delivery due to a shape memory effect that is achieved upon subjecting the expandable components to an activating stimulus.

Vaso-occlusive coils, also known as embolic coils, are a commonly utilized class of vaso-occlusive devices. Vaso-occlusive coils are commonly made from a biocompatible material, such as biocompatible metal, to minimize problems associated with tissue irritation and rejection. These coils are often shaped as complex three dimensional curves that fill in portions of a blood vessel's lumen and slow blood flow through the same. As a specific example, in the treatment of an aneurysm, an embolic coil is inserted into the affected blood vessel using a catheter, and is placed within the bulging, weakened section of the blood vessel. When in place, the coil forms its operational size and shape, and slows down the flow of blood through the weakened section. Over time, a clot forms around the embolic coil, and blood flow through the weakened section is completely blocked. Thus, failure of this weakened section is less likely, and the resulting hemorrhage may be prevented.

Vaso-occlusive coils are typically made from stainless steel, platinum, or titanium wire allowing them to be visible via X-ray and be flexible enough to conform to the aneurysm shape. One example of a vaso-occlusive coil is a Guglielmi Detachable Coil, or GDC. The GDC is a platinum coil commonly used in intracranial non-invasive surgery for the occlusion of brain aneurysms. The GDC system consists of a soft platinum GDC coil soldered to a stainless steel delivery wire. Platinum coils are distinctive in that the material can be easily bent and subsequently regain its original coil shape. Electrical current is used to dissolve the stainless steel delivery wire proximal to the platinum coil by means of electrolysis. Once electrolysis occurs, the delivery wire can be removed, leaving the GDC coil in place. Mechanically detachable coils and other electronically detachable coils are also currently available.

Vaso-occlusive coils are commonly constructed by winding a wire strand about a first, relatively small diameter mandrel, followed by heat treating, to give it a "primary" helical coil shape. The helical coil is then typically wound around another mandrel, followed by further heat treating, in order to produce a "secondary" shape. Often, polymeric fiber bundles are added to the metallic coil to enhance the coil's thrombogenicity (i.e., its ability to cause the formation of clots). The fiber bundles, however, take up a significant amount of space within the delivery device causing significant resistance during delivery.

As previously indicated, in the present disclosure, vaso-occlusive devices are provided which comprise one or more expandable components that have a low profile during delivery but which expand laterally outward subsequent to device delivery due to a shape memory effect.

A material is said to exhibit a shape memory effect if it can be fixed into a temporary shape and subsequently approach or completely return to an original (or "permanent" or "memorized") shape upon exposure to a suitable activating stimulus. Suitable activating stimuli include a force whereby an expandable component that is compressed into a confined space is forced from the confined space and expands laterally outward to approach or completely return to an original shape (in which case the expandable component is an elastic component that behaves like a compressed spring). Suitable activating stimuli also include thermal stimulus, electrical stimulus, chemical stimulus, pressure stimulus, and light stimulus, among others, that cause the material to approach or completely return to an original shape.

A change in shape caused by a change in temperature is called a thermally induced shape memory effect. In the present disclosure, thermally activated shape memory materials may be selected for which a shape change in the material occurs at thermal transition temperatures somewhat greater than room temperature (25° C.), and somewhat greater than normal body temperature (37° C.) in various embodiments, for example, having thermal transition temperatures ranging from 30° C. to 60° C. or more, for instance, ranging from 30° C. to 32° C. to 34° C. to 36° C.

to 37° C. to 38° C. to 40° C. to 42° C. to 45° C. to 50° C. to 55° C. to 60° C. (i.e., ranging between any two of the preceding numerical values).

Certain metals are known to exhibit a thermally induced shape memory effect, of which nickel-titanium alloys known as nitinol are perhaps the best known. Nitinol shape memory alloys can exist in a two different temperature-dependent crystal structures (phases) called martensite (lower temperature phase) and austenite (higher temperature or parent/permanent phase). When martensite nitinol is heated, it begins to change into austenite. The temperature at which this phenomenon starts is called austenite start temperature (As). The temperature at which this phenomenon is complete is called austenite finish temperature (Af). On the other hand, when austenite Nitinol is cooled, it begins to change into martensite. The temperature at which this phenomenon starts is called martensite start temperature (Ms). The temperature at which martensite is completely reverted is called martensite finish temperature (Mf). Composition and metallurgical treatments can impact these temperatures.

Generally, the shape memory effect allows the alloy to be (a) provided in a first configuration while in the relative high-temperature austenite phase, (b) cooled below a transition temperature range, for example, from Ms down to Mf or below, whereupon the austenite is partially (between Ms and Mf) to completely (at Mf or below) transformed into the relative low-temperature martensite phase, (c) deformed while at the cooled temperature into a second configuration, and (d) heated back to the austenite transition temperature range, specifically from As up to Af or above, such that the alloy transforms partially (between As and Af) to completely (at Af or above) from the second configuration back to the first configuration. In certain embodiments, vaso-occlusive devices are provided which comprise one or more expandable components that have a low profile during delivery but which expand laterally outward subsequent to device delivery, due to a shape memory effect, wherein the expandable components are formed using a shape memory metal, for example, nitinol.

In the present disclosure, an expandable component may have a first shape corresponding to a contracted profile when the nitinol shape memory material is in the martensite phase and a second shape corresponding to an expanded profile when the shape memory material is in the austenite phase. A vaso-occlusive device comprising the expandable component may be advanced to an implant location in a patient when the shape memory material is in the martensite phase and the expandable component has the first shape, under conditions such that the shape memory material remains at a temperature that is below the thermal transition temperature of the shape memory material (e.g., below As). The vaso-occlusive device is then delivered to the implant location under conditions such that the temperature of the shape memory material rises above the thermal transition temperature of the shape memory material (e.g., above As), with the result being that the shape memory material transitions partially (i.e., at temperatures between As and Af) or completely (i.e., at temperatures at Af or above) to the austenite phase and the expandable component changes partially or completely from the first shape to the second shape. This results in the transition of the expandable component from the contracted profile to the expanded profile at the time of implantation.

Various polymers are also known to exhibit a thermally induced shape memory effect. With shape memory polymers, the process of programming and recovery of a shape is generally as follows: (a) first, the polymer is conventionally processed to receive its original, or permanent, shape, (b) the polymer is then deformed and the intended temporary shape is fixed in a process called programming, which typically consists of heating the sample above a thermal transition temperature, deforming it, and cooling it below the transition temperature while in the deformed state. The permanent shape is now stored while the sample shows the temporary shape. Subsequent heating of the shape memory polymer above the transition temperature leads to the recovery of the stored, permanent shape. Dimensional changes within shape memory polymer may be on the order of, for example, 100-1000%.

Specific examples of shape memory polymers include block copolymers and covalently linked polymer networks. These polymers may exhibit a shape memory functionality by using the polymer chains as a type of molecular switch. One possibility for a switch function is a thermal transition of the chains in the temperature range of interest for a particular application. At temperatures above the thermal transition temperature (Ttrans) the chain segments become more flexible, whereas the flexibility of the chains below this thermal transition is at least partly limited.

Phase-segregated multiblock copolymers, commonly linear block copolymers, are known to display at least two separated phases. The phase showing the highest thermal transition Tperm (sometimes referred to as the hard phase) provides physical cross-links (also referred to sometimes as "physical netpoints") and is responsible for the permanent shape of the material. (Above this temperature the polymer commonly melts and can be processed by conventional processing techniques such as extrusion, injection molding, melt spinning, etc.) The portion of the block copolymer that forms the hard phase is sometimes referred to as the hard segment. A second phase (i.e., a switching phase) enables the fixation of the temporary shape. The portion of the block copolymer that forms the switching phase is sometimes referred to as the switching segment. The transition temperature (Ttrans) for the fixation of the switching phase is typically either a glass transition temperature (Tg) or a melting temperature (Tm). In the case of a melting temperature, one observes a relatively sharp transition in most cases, whereas glass transitions typically extend over a broader temperature range. After applying a force that is sufficient to deform the material at a temperature above Ttrans but below Tperm, a temporary shape is achieved, which can be fixed by cooling the polymer below Ttrans while continuing to apply the deformation force. The deformation force may then be removed. Subsequent heating of the material above Ttrans returns the material to its permanent shape.

Unlike the physical crosslinks for the above block copolymers, the permanent shape of shape memory polymer networks are stabilized via covalent crosslinks. Besides the crosslinks, such networks also generally contain flexible components in the form of amorphous chains. If the working temperature is above the Ttrans for these chains, the networks will be elastic. As with shape memory block copolymers, the Ttrans thermal transition chosen for the fixation of the temporary shape may be a melting point or a glass transition temperature. After deforming the material at a temperature above the Ttrans, the temporary deformed shape can be fixed by cooling the polymer below Ttrans. Subsequent heating of the material above Ttrans returns the material to its permanent shape.

Further information on shape memory polymers can be found, for example, in U.S. Patent Application Pub. No.

2010/0069838 to Weber et al. and in A. Lendlein and S. Kelch, "Shape Memory Polymers," *Angew. Chem. Int. Id.* 2002, 41, 2034-2057.

In various embodiments, vaso-occlusive devices are provided which comprise one or more expandable components, formed using a shape memory polymer, which have a contracted profile during delivery but which transition to an expanded profile subsequent to device delivery due to a shape memory effect. A vaso-occlusive device comprising such expandable components may be advanced to an implant location in a patient under conditions such that the shape memory polymer remains at a temperature that is below the transition temperature of the shape memory polymer and such that the shape memory polymer remains in a first temporary shape. The vaso-occlusive device is then released at the implant location under conditions such that the temperature of the shape memory polymer rises above the transition temperature of the shape memory polymer, with the result being that the shape memory polymer transitions from the first temporary shape to a second permanent shape. This results in the transition of the one or more expandable components from the contracted profile to the expanded profile at the time of implantation.

By providing vaso-occlusive devices which comprise a device portion and one or more expandable components that comprise a shape memory material, the one or more expandable components can be shaped to provide an initial low profile configuration (i.e., a configuration of reduced cross-sectional area), for example, by conforming the components to a surface of an underlying device portion. The expandable components, however, expand outward from the device portion upon being subjected to a suitable activating stimulus, for example, an increase in temperature from below a thermal transition temperature of the shape memory material to above the thermal transition temperature of the shape memory material. In this way, the present disclosure provides vaso-occlusive devices that comprise one or more expandable components that have a low profile during delivery but which expand laterally outward subsequent to device delivery due to a shape memory effect.

As previously noted, an advantage of such a device is that it allows the device to be advanced into the vasculature in a low resistance, low profile configuration (i.e., a configuration of reduced cross-sectional area) that enables or improves delivery of the device through a constrained space (e.g., blood vessel, catheter, etc.), after which the expandable components are expanded outward, thereby increasing the cross-sectional area of the device and thus enhancing the ability of the device to form an occlusion.

In this way, vaso-occlusive devices of the present disclosure may be used to stop undesired blood flow in a variety of circumstances, for example, to stop or prevent bleeding aneurysms, to stop abnormal blood flow in arteriovenous malformations (AVMs), to close a patent ductus arteriosus (PDA), to treat traumatic fistulae, or to perform tumor embolization, among other uses. In various embodiments, the diameter or the body lumen being treated by the device is substantially larger than the diameter of the device. For instance, in the case of an embolic coil, the coil may form a looped or multi-looped structure within the body lumen (e.g., aneurysm, etc.). Moreover, multiple coils may be introduced to the treatment site.

As noted above, in various embodiments, the expandable components are formed using a shape memory material which has a transition temperature at body temperature or just below body temperature (e.g., in the range of 30° C. to 37° C.). For example, the shape memory material may be a shape memory metal or polymer which has a first temporary shape at ambient temperature (e.g., 25° C.) and which has transitions to a second permanent shape at some point within the range of 30° C. to 37° C.

In various embodiments, the shape memory material may be a nitinol alloy. The device may be configured such that the expandable components are in a configuration corresponding to an expanded device configuration when the shape memory metal is in the austenite phase. After cooling the shape memory metal such that it is transformed from the austenite phase to the martensite phase, the expandable components may be placed in a configuration corresponding to a contracted device configuration by deformation of the shape memory metal (e.g., by crimping, folding, wrapping, etc.). Upon warming the device above the transition temperature, however, the device takes on an expanded device configuration.

In various embodiments, the shape memory material may be a shape memory polymer. The device may be configured such that the expandable components are in a configuration corresponding to an expanded device configuration when the shape memory polymer is in its permanent shape. The shape memory polymer may be fixed in a temporary shape corresponding to a contracted device configuration via a programming step, which typically consists of heating the shape memory polymer above its transition temperature, deforming it to the temporary shape, and cooling it below the transition temperature while in the deformed temporary shape. The permanent shape is now stored while the sample shows the temporary shape. Subsequent heating of the shape memory polymer above the transition temperature leads to the recovery of the stored, permanent shape and thus expansion of the expandable components.

In various embodiments, it may be desirable to cool the device during delivery, for example, by flowing a cooled liquid, such as cooled saline or cooled contrast medium, through a catheter containing the device during delivery, to ensure that the device remains below the thermal transition temperature of the shape memory material.

In various embodiments, a shape memory material (e.g., a nitinol shape memory alloy or a shape memory polymer) is provided which has transition temperature that is slightly above body temperature (e.g., in the range of 38° C. to 60° C.), in which case the shape memory material is heated to above the transition temperature (e.g., by resistance heating, by introduction of a warm/hot fluid, or by application of radiated energy such as infrared energy, light, UV energy or RF energy, among other strategies) after delivery to a placement site. This heating causes the expandable components to revert to a memorized configuration corresponding to an expanded device configuration. In these embodiments, the elevated temperature of the shape memory material may enhance clotting associated with the device.

In various embodiments, the one or more expandable components are associated with a device substrate, more typically, an elongated device substrate. The device substrate may be, for example, a vascular plug, an occlusive basket, or a vaso-occlusive coil. As previously indicated, vaso-occlusive coils may be made, for example, from a suitable metal wire, such as stainless steel, platinum, or titanium wire, allowing the coils to be visible via X-ray and be flexible enough to conform to tissue at the placement site (e.g., an aneurysm, etc.).

The one or more expandable components may be associated with the device substrate in a variety of ways, including the use of adhesives, solders, or spot welds, by snapping or tying the expandable component onto the device substrate, or by the integration of the expandable components into the cut pattern of an underlying substrate (e.g., an underlying nitinol or shape memory polymer), among others.

The expandable components may be, for example, in the form of a sheet of material that is wrapped or curled around a device substrate (e.g., wrapped or curled in the form of a cylinder or partial cylinder) and which unwraps or uncurls to an expanded "memorized" form when the transition temperature is passed. In a specific embodiment, as shown schematically in FIG. 1A, the expandable component 110 may be in a substantially cylindrical form, which reverts to a more planar "memorized" form, as shown schematically in FIG. 1B. In FIG. 1A, a partial cylinder is formed which spans a majority of a full cylinder circumference (360°). However, the amount of wrap may range from, for example, from 90° or less to 360° or more, for instance ranging from 90° to 105° to 120° to 135° to 150° to 165° to 180° to 195° to 210° to 225° to 240° to 255° to 270° to 285° to 300° to 315° to 330° to 345° to 360° (i.e., ranging between any two of the preceding numerical values).

Figure 1B:
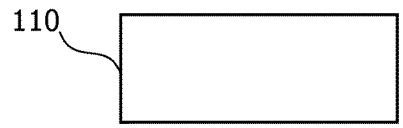
Figure 2A:
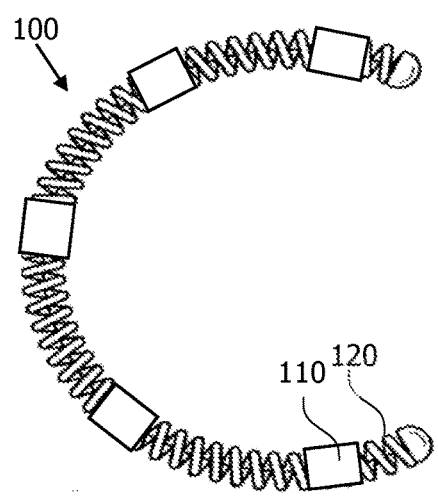
FIG. 2A is a schematic illustration of a vaso-occlusive coil having a plurality of expandable components disposed along its length in a low profile, according to an embodiment of the present disclosure.
Figure 2B:
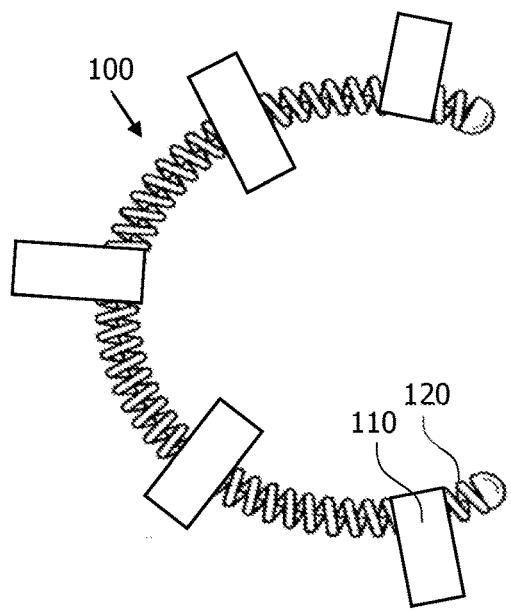
FIG. 2B is a schematic illustration of the vaso-occlusive coil of FIG. 2A after expansion of the expandable components.

FIG. 2A shows expandable components 110 of a type like that of FIGS. 1A-1B associated with a vaso-occlusive coil 120. The expandable components 110 are shown wrapped around at least a portion of the coil 120 so as to substantially conform to the outer surface of the coil 120. When the transition temperature is passed, each expandable component 110 uncurls into a substantially planar configuration as shown schematically in FIG. 2B. Three of the expandable components 110 are shown connected to the coil 120 near one end of the expandable component, whereas two of the expandable components 110 are connected to the coil 120 at the center of the expandable component, among many other possible attachment strategies.

Figure 3:
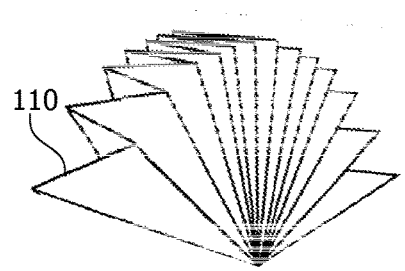
FIG. 3 is a schematic illustration of an expandable component, according to an embodiment of the present disclosure.

In various embodiments, the expandable components 110 may be folded for delivery and then partially or completely unfolded to a memorized shape on delivery. For example, the memorized shape may be the shape of a fan as shown in FIG. 3, which can be collapsed (e.g., folded) into a substantially flat profile during delivery and then expanded into a fan-like shape as shown.

In various embodiments, the expandable components 110 may be formed from wire-like elements that allow for expansion when the elements are straightened. Such expandable components 110 may comprise, for example, undulating (e.g., zig-zag, serpentine, etc.) elements. An example of such an expandable component 110 is shown in partial view in FIG. 4A. When the elements are straightened to any degree, for example, as shown in FIG. 4B, the length (and overall area) of the expandable component 110 increases. Various patterns of this type may be adopted from the stent art.

Figure 4A:
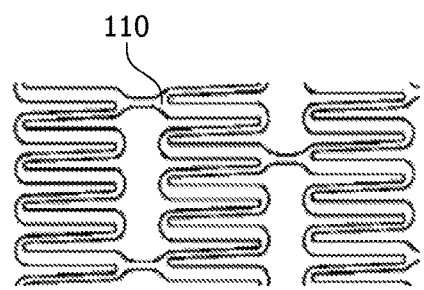
FIG. 4A and FIG. 4B are schematic illustrations of a portion of an expandable component in contracted and expanded configurations, respectively, according to an embodiment of the present disclosure.
Figure 4B:
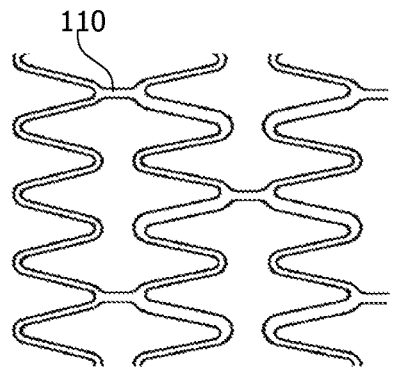

In some embodiments, an expandable component 110 like that shown in FIG. 4A may be at least partially wrapped around a device substrate circumference to further reduce the delivery diameter of the expandable component 110. Where wrapped in this fashion, the expandable component 110 component may unwrap to a more planar orientation while at the same time lengthening as shown in FIGS. 4A-4B. In these embodiments, wrapped expandable components are analogous to a portion of an expandable stent, which extends around at least a portion of a full 360° circumference of the device substrate, for example, wrapping around a portion of the device substrate circumference ranging from 90° or less up to nearly 360°, for instance, ranging from 90° to 105° to 120° to 135° to 150° to 165° to 180° to 195° to 210° to 225° to 240° to 255° to 270° to 285° to 300° to 315° to 330° to 345° to 359° (i.e., ranging between any two of the preceding numerical values).

In some embodiments, the expandable component 110 is in the shape of a tube and has a full circumference of 360° analogous to a complete stent, thereby expanding from a contracted diameter to an expanded diameter at the time of deliver.

Figure 5A:
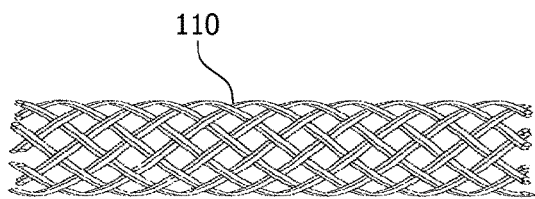
FIG. 5A and FIG. 5B are schematic illustrations of an expandable component in contracted and expanded configurations, respectively, according to an embodiment of the present disclosure.
Figure 5B:
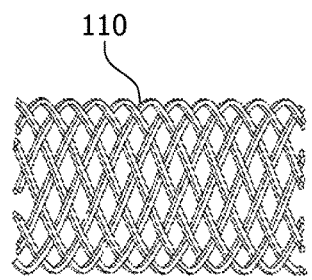

In some embodiments, the expandable component is one wherein two sets of strands (e.g., wires, ribbons, etc.) are helically wound in opposite directions to form a cylindrical braid (or portion thereof), sometimes referred to as a biaxial braid. One specific example, is the expandable component 110 shown in FIGS. 5A and 5B which illustrates a cylindrical braid in which two sets of fibers (paired fibers are shown) are formed into helices which are wound and braided in opposite directions. As seen by comparing FIGS. 5A and 5B, by increasing the angle of intersection of the oppositely wound strands, an increase in expandable component 110 diameter is achieved (along with a simultaneous decrease in expandable component 110 length).

For example, one or more expandable components 110 may have a temporary configuration in which the oppositely wound strands intersect at a relatively small angle of intersection corresponding to a relatively small diameter (see, e.g., FIG. 5A) such that the expandable components are snugly fitted around the diameter of an elongated device substrate such as a vaso-occlusive coil for delivery. Subsequently, the expandable component 110 is subjected to an activating stimulus such that the expandable components revert to a permanent configuration where the oppositely wound strands have an increased angle of intersection and an increased diameter (see, e.g., 5B) as a result of the shape memory process.

In some embodiments, the expandable component may be in the form of a partial cylinder which only extends around a portion of a full 360° circumference of the device substrate, for example, having a partial circumference ranging from 90° or less up to nearly 360°, for instance, ranging from 90° to 105° to 120° to 135° to 150° to 165° to 180° to 195° to 210° to 225° to 240° to 255° to 270° to 285° to 300° to 315° to 330° to 345° to 359° (i.e., ranging between any two of the preceding numerical values).

In some embodiments, a plurality of cylindrical braids, which have a temporary shape having a relatively small diameter and a memorized shape having an increased diameter, are attached to an outer surface of the device substrate (i.e., the device substrate does not pass through the center of the cylinders).

Figure 6A:
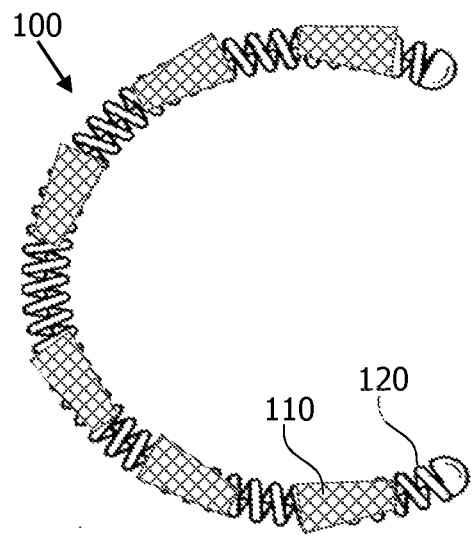
FIG. 6A is a schematic illustration of a vaso-occlusive coil having a plurality of expandable components disposed along its length in a low profile, according to an embodiment of the present disclosure.
Figure 6B:
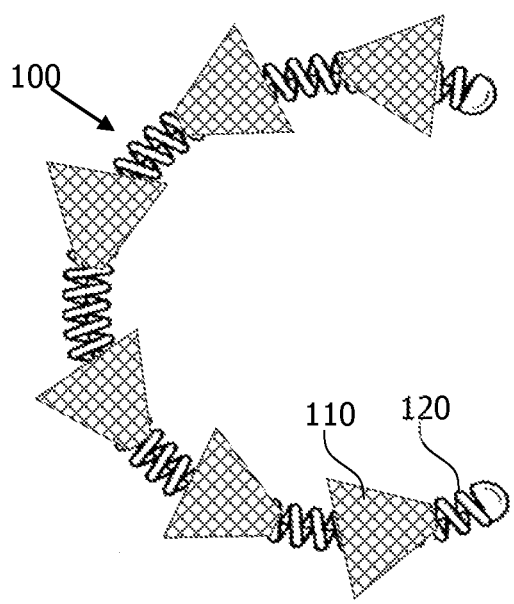
FIG. 6B is a schematic illustration of the vaso-occlusive coil of FIG. 6A after expansion of the expandable components.

Using the above and analogous strategies, expandable components 110 in a wide range of shapes can be formed. For example, in the embodiment shown in FIG. 6A, expandable components 110 may be employed in conjunction with a vaso-occlusive coil 120. When the transition temperature is passed, the components 110 open in a fan-like manner as shown in FIG. 6B.

In various embodiments, expandable components may be formed of thin-film materials (e.g., thin-film metals or polymers) which may be formed, for example, via a suitable coating or deposition process. If an expandable component other than a solid sheet is desired, the material may be masked and/or etched using a suitable technology (e.g., using technologies well-known in the semiconductor art) or may be cut using a suitable technology (e.g., mechanical cutting, laser cutting, etc.) to produce a near infinite range of structural elements. As one example, structural elements like those shown in FIGS. 4A-4B, among many others, may be readily formed using processes of this nature.

In various embodiments, the expandable components 110 of the present disclosure may be coated with a thrombogenic material that enhances thrombus formation/clotting. Examples of such materials include thrombin, collagen, fibrinogen, vitronectin, gelatin, trypsin, protamine, polylysine, tissue factor, von Willebrand factor (vWF), arachidonic acid, lysophosphatidic acid, thromboxane, coagulation factors, adhesion molecules, plasminogen activator inhibitor, tumor necrosis factor alpha, and interleukin-1.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A vaso-occlusive device comprising an elongated device portion and one or more expandable components which comprise a shape memory material and which expand laterally outward from the elongated device portion upon being subjected to an increase in temperature from below a thermal transition temperature of the shape memory material to above the thermal transition temperature of the shape memory material.

2. The vaso-occlusive device of claim 1, wherein the elongated device portion comprises an elongated cylindrical portion.

3. The vaso-occlusive device of claim 1, wherein the elongated device portion comprises a slotted tube or a coil.

4. The vaso-occlusive device of claim 1, wherein the thermal transition temperature of the shape memory material is between 30° C. and 37° C. or wherein the thermal transition temperature of the shape memory material is between 38° C. and 50° C.

5. The vaso-occlusive device of claim 1, wherein the shape memory material is a shape memory alloy.

6. The vaso-occlusive device of claim 1, wherein the shape memory material is a shape memory polymer.

7. The vaso-occlusive device of claim 1, wherein the expandable component comprises a sheet of the shape memory material.

8. The vaso-occlusive device of claim 7, wherein the sheet of the shape memory material is folded at a surface of the elongated device portion, or wherein the sheet of the shape memory material is at least partially wrapped around the elongated device portion.

9. The vaso-occlusive device of claim 7, wherein the sheet of shape memory material comprises a plurality of apertures.

10. The vaso-occlusive device of claim 1, wherein the expandable component comprises a plurality of elongated segments of shape memory material.

11. The vaso-occlusive device of claim 10, wherein the elongated segments form an undulating pattern.

12. The vaso-occlusive device of claim 10, wherein each of the elongated segments is in the form of a helix or a portion thereof.

13. The vaso-occlusive device of claim 10, comprising a plurality of the elongated segments forming oppositely wound helixes or portions thereof.

14. The vaso-occlusive device of claim 1, wherein the expandable components are provided with a coating of thrombogenic material.

15. A vaso-occlusive system comprising (a) a vaso-occlusive device comprising an elongated device portion and one or more expandable components which comprise a shape memory material and which expand laterally outward from the elongated device portion upon being subjected to an increase in temperature from below a thermal transition temperature of the shape memory material to above the thermal transition temperature of the shape memory material and (b) a catheter configured to introduce said vaso-occlusive device into the vasculature.

16. A method of forming a vascular occlusion comprising: (a) advancing a vaso-occlusive device to an implant location in a subject, said vaso-occlusive device comprising an elongated device portion and one or more expandable components which comprise a shape memory material and which expand laterally outward from the elongated device portion upon being subjected to an activating stimulus, the stimulus being an increase in temperature from below a thermal transition temperature of the shape memory material to above the thermal transition temperature of the shape memory material and (b) delivering the vaso-occlusive device to said implant location under conditions such that an activating stimulus is applied to the device and the expandable components expand laterally outward from the elongated device portion.

17. The method of claim 16, wherein the vaso-occlusive device is advanced to the implant location under conditions such that the shape memory material is at a temperature that is below the thermal transition temperature of the shape memory material, and wherein the vaso-occlusive device is delivered at the implant location under conditions such that the temperature of the shape memory material rises above the thermal transition temperature of the shape memory material thereby expanding the expandable components.

18. The method of claim 17, wherein a body temperature of the subject is above the transition temperature of the shape memory material or wherein a body temperature of the subject is below the transition temperature of the shape memory material and the shape memory material is heated to above the transition temperature of the shape memory material upon delivery.

19. The method of claim 17, wherein the shape memory material is a shape memory polymer or a shape memory alloy.

* * * * *